(12) United States Patent
Kishida

(10) Patent No.: US 12,172,009 B2
(45) Date of Patent: Dec. 24, 2024

(54) ELECTROTHERAPY DEVICE

(71) Applicant: KANEKA CORPORATION, Osaka (JP)

(72) Inventor: Manabu Kishida, Okaya (JP)

(73) Assignee: KANEKA CORPORATION, Osaka (JP)

( * ) Notice: Subject to any disclaimer, the term of this patent is extended or adjusted under 35 U.S.C. 154(b) by 934 days.

(21) Appl. No.: 17/279,790

(22) PCT Filed: Aug. 16, 2019

(86) PCT No.: PCT/JP2019/032095
§ 371 (c)(1),
(2) Date: Mar. 25, 2021

(87) PCT Pub. No.: WO2020/075387
PCT Pub. Date: Apr. 16, 2020

(65) Prior Publication Data
US 2021/0330966 A1 Oct. 28, 2021

(30) Foreign Application Priority Data
Oct. 12, 2018 (JP) .................................. 2018-193126

(51) Int. Cl.
*A61N 1/32* (2006.01)
*A61M 37/00* (2006.01)
*A61N 1/05* (2006.01)

(52) U.S. Cl.
CPC .............. *A61N 1/327* (2013.01); *A61M 37/00* (2013.01); *A61N 1/0502* (2013.01); *A61M 2037/0007* (2013.01)

(58) Field of Classification Search
CPC ...... A61N 1/327; A61N 1/0502; A61N 1/325; A61M 37/00; A61M 2037/0007; A61B 18/1482; A61B 2018/143; A61B 2018/1475
See application file for complete search history.

(56) References Cited

U.S. PATENT DOCUMENTS

2015/0328449 A1* 11/2015 Soden .............. A61B 17/00234
604/20

FOREIGN PATENT DOCUMENTS

| JP | 2004-41434 A | 2/2004 |
|----|--------------|--------|
| JP | 2016-500329 A | 1/2016 |

OTHER PUBLICATIONS

International Search Report, issued in PCT/JP2019/032095, PCT/ISA/210, dated Oct. 21, 2019.

\* cited by examiner

*Primary Examiner* — Chelsea E Stinson
*Assistant Examiner* — Anh Bui
(74) *Attorney, Agent, or Firm* — Birch, Stewart, Kolasch & Birch, LLP

(57) ABSTRACT

Provided is an electrotherapy device suitably used in electroporation method, and specifically configured to inject medicine and the like into deep inside of the body. The electrotherapy device has an outer shaft having a lumen and extending in a distal-proximal direction; an inner shaft disposed in the lumen of the outer shaft; a needle tube fixed to the inner shaft; and at least one linear conductor having at least one electrode needle fixed to the inner shaft and having at least one conductive line connected to a proximal part of the electrode needle, the needle tube and the electrode needle configured to project or retract from a distal part of the outer shaft.

13 Claims, 5 Drawing Sheets

[Fig. 1]
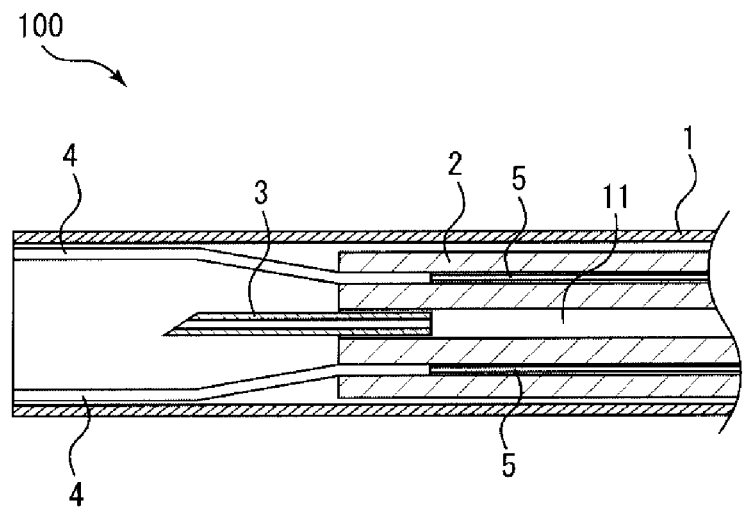
[Fig. 2]
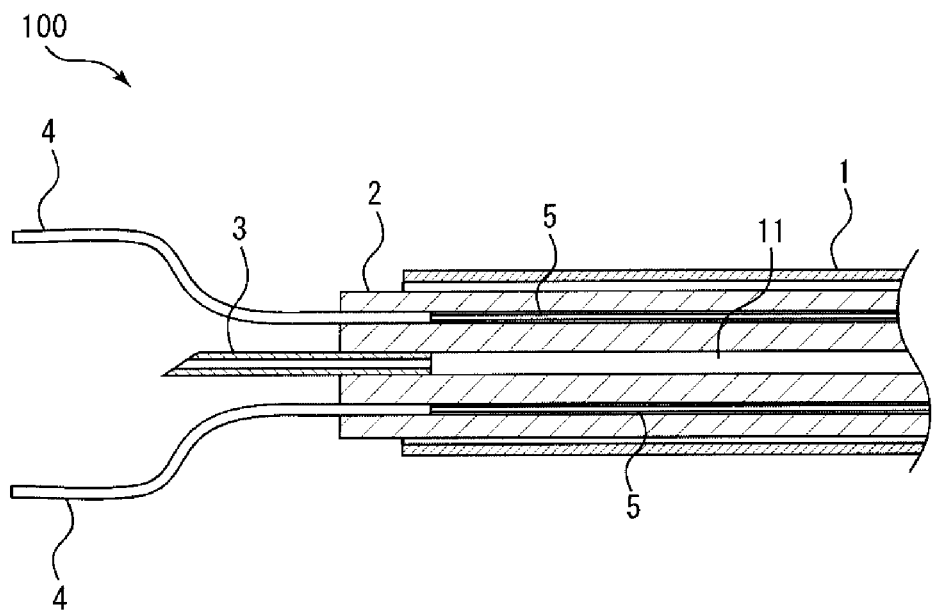

[Fig. 3]
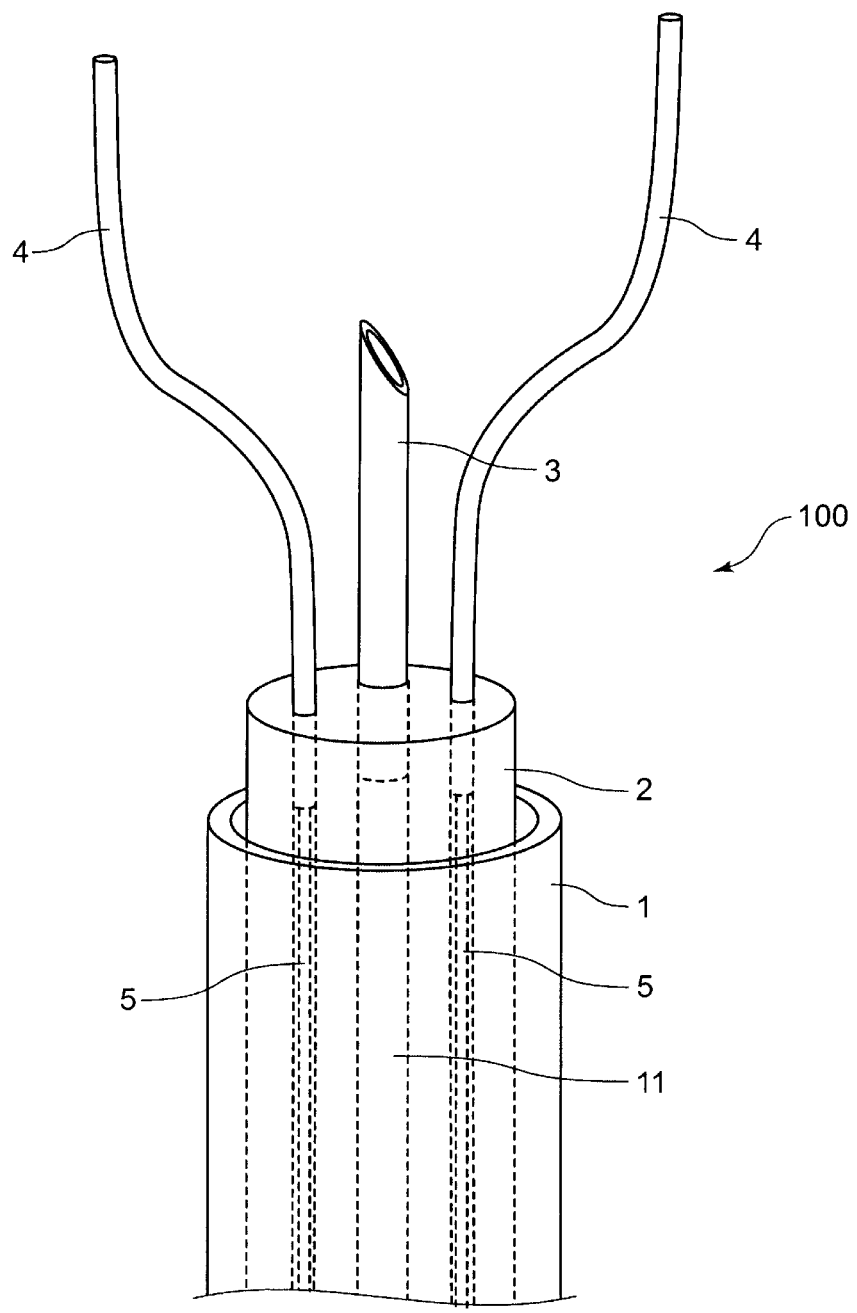

[Fig. 4]
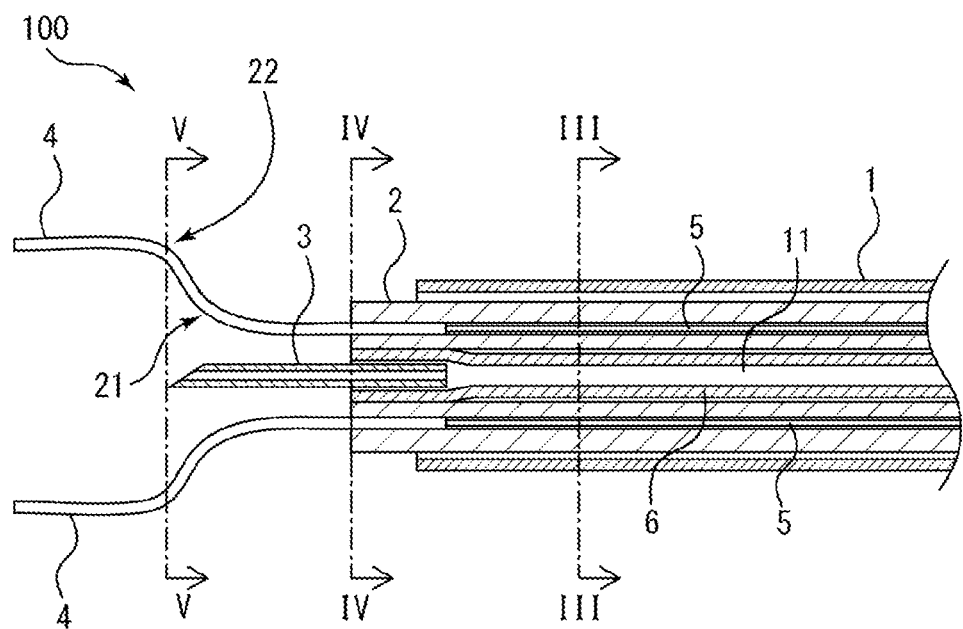
[Fig. 5A]
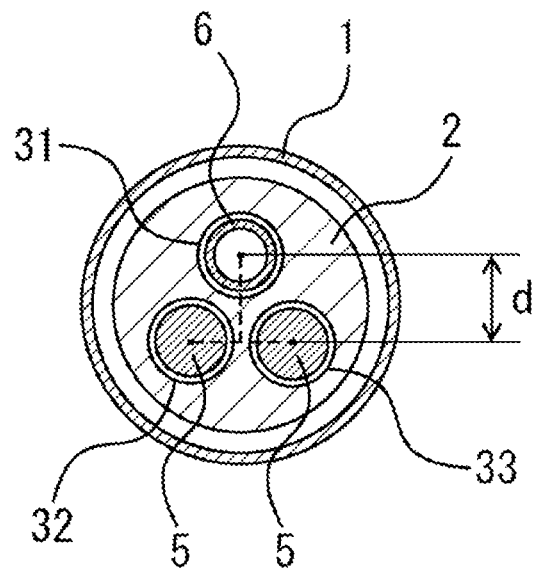

[Fig. 5B]
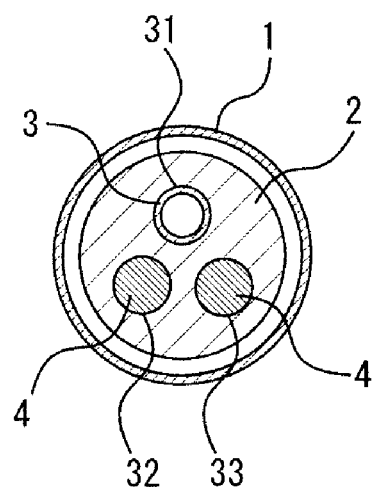

[Fig. 5C]
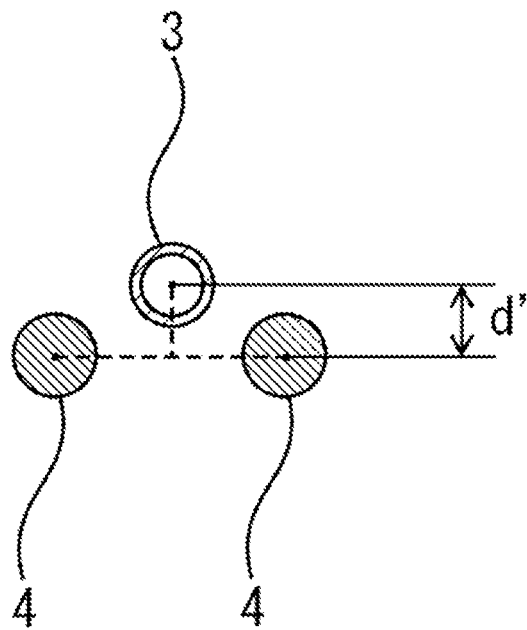
[Fig. 6]
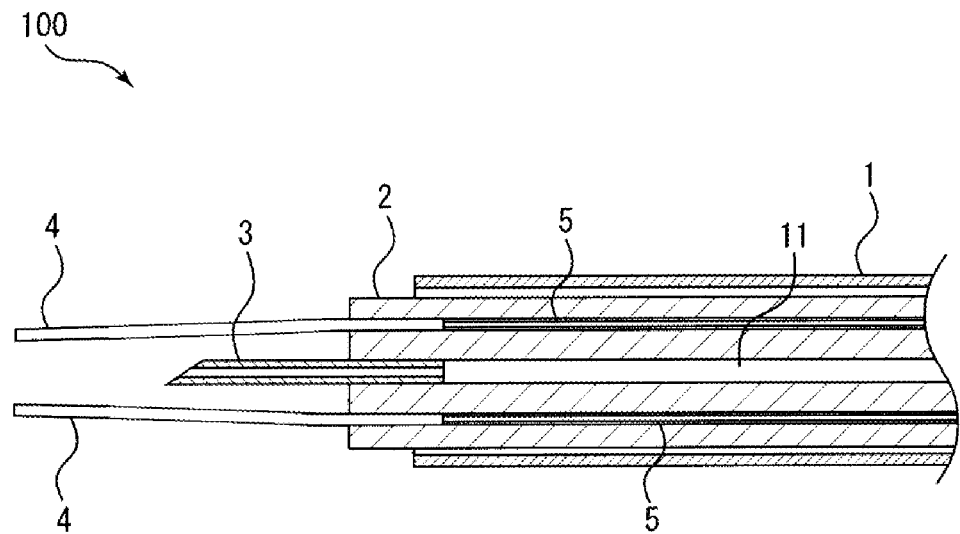

ELECTROTHERAPY DEVICE

TECHNICAL FIELD

The present invention relates to an electrotherapy device. In particular, the present invention relates to an electrotherapy device having an electrode needle applying high-frequency wave to biological tissue and a needle tube injecting medicine and the like to biological tissue.

BACKGROUND ART

Electroporation method is known as a method where it becomes easy for medicine and the like to permeate biological tissue including cells by injecting medicine and the like while applying electrical field to bipolar electrodes. As an electrotherapy device used in such a method, an electroporation device having a plurality of electrodes is disclosed in patent document 1. The electroporation device disclosed in the patent document 1 has a pair of electrodes that is stored being capable of projecting and retracting from an end part of a guide tube and applies DC pulses generated by means for applying pulses. The patent document 1 discloses that medicine, genes, or the like are distributed to a localized area such as a malignant tumor by local injection, intraarterial injection, or intravenous injection, and then DC pulses are applied to the area.

RELATED ART DOCUMENT

Patent Document

Patent Document 1: JP-A-2004-041434

SUMMARY OF THE INVENTION

Problems to be Solved by the Invention

The device disclosed in the patent document 1 can place the electrode at a position such as a body surface, which is easy to be accessed, and inject medicine and the like to the body surface before or while applying electrical field to an intended area, however, it cannot inject medicine and the like into deep inside of the body.

The present invention has been achieved focusing on the circumstances described above, and the purpose thereof is to offer an electrotherapy device that can be suitably used for the electroporation method, and especially can inject medicine and the like into deep inside of the body.

Means for Solving the Problems

An electrotherapy device according to the present invention has the following constitution to solve the above problems.

The electrotherapy device comprises an outer shaft having a lumen and extending in a distal-proximal direction; an inner shaft disposed in the lumen of the outer shaft; a needle tube fixed to the inner shaft; and at least one linear conductor having at least one electrode needle fixed to the inner shaft and having at least one conductive line connected to a proximal part of the electrode needle, and the needle tube and the electrode needle configured to project or retract from a distal part of the outer shaft.

Effects of the Invention

The electrotherapy device according to the present invention has a configuration in which the needle tube and the electrode needle are fixed to the inner shaft disposed in the lumen of the outer shaft and the needle tube and the electrode needle are configured to project or retract from the distal part of the outer shaft, and therefore, it can inject medicine and the like into deep inside of the body and also apply electrical field from the electrode needle to an intended area.

BRIEF DESCRIPTION OF THE DRAWINGS

FIG. 1 is a cross-sectional view of a constitutional example of a distal part of an electrotherapy device according to the present invention, showing a condition where a needle tube and an electrode needle are not projected from a distal part of an outer shaft.

FIG. 2 is a cross-sectional view of a distal part of the electrotherapy device shown in FIG. 1, showing a condition where the needle tube and the electrode needle are projected from the distal part of the outer shaft.

FIG. 3 is a perspective view of a distal part of the electrotherapy device shown in FIG. 2.

FIG. 4 is a cross-sectional view of another constitutional example of a distal part of an electrotherapy device according to the present invention, showing a condition where a needle tube and an electrode needle are projected from a distal part of an outer shaft.

FIG. 5A is a cross-sectional view taken along the line III-III of FIG. 4,

FIG. 5B is a cross-sectional view taken along the line IV-IV of FIG. 4, and

FIG. 5C is a cross-sectional view taken along the line V-V of FIG. 4.

FIG. 6 is a cross-sectional view of another constitutional example of a distal part of an electrotherapy device according to the present invention, showing a condition where a needle tube and an electrode needle are projected from a distal part of an outer shaft.

MODE FOR CARRYING OUT THE INVENTION

An electrotherapy device according to the present invention comprises an outer shaft having a lumen and extending in a distal-proximal direction; an inner shaft disposed in the lumen of the outer shaft; a needle tube fixed to the inner shaft; and at least one linear conductor having at least one electrode needle fixed to the inner shaft and having at least one conductive line connected to a proximal part of the electrode needle, and the needle tube and the electrode needle configured to project or retract from a distal part of the outer shaft. The electrotherapy device can inject medicine and the like into deep inside of the body and also apply electrical field from the electrode needle to an intended area thanks to a configuration where the needle tube and the electrode needle fixed to the inner shaft disposed in the lumen of the outer shaft are configured to project or retract from the distal part of the outer shaft.

Hereinafter, the electrotherapy device according to the present invention will be specifically described in reference to figures, however, the present invention is not limited to the figures and can be put into practice after appropriate modifications within a range meeting the gist of the above and the below, all of which are to be encompassed within the technical scope of the present invention. Note that a proximal side means the side of an operator's hand of the electrotherapy device, and a distal side means the side opposite to the side of an operator's hand.

FIG. 1 and FIG. 2 are schematic cross-sectional views of one example of an embodiment of an electrotherapy device 100 according to the present invention, both of which show a distal part of the electrotherapy device.

In FIG. 1 and FIG. 2, an outer shaft 1 has an lumen and extends in a distal-proximal direction, and an inner shaft 2 is disposed in the lumen of the outer shaft 1. To a distal part of the inner shaft 2, a needle tube 3 and an electrode needle 4 are fixed. The needle tube 3 and/or the electrode needle 4 may be directly or indirectly fixed to the inner shaft 2. The form of fixing is not particularly limited, and they may be fixed with a member for fixing or adhesive, or may be fixed by thermal fusion bonding or press fitting. A distal end of the inner shaft 2 may be closed at a position other than a position where the needle tube 3 and the electrode needle 4 of the linear conductor are disposed, which can prevent body fluid and the like from infiltrating the inside of the inner shaft 2.

A lumen 11, which is a penetration duct, is formed in the inner shaft 2, and the lumen 11 is connected to a proximal end part of the needle tube 3. By connecting the lumen 11 and the needle tube 3 to each other, medicine and the like can be injected into deep inside of the body from the side of an operator's hand of the electrotherapy device 100 through the lumen 11 and the needle tube 3.

A conductive line 5 is connected to the proximal part of the electrode needle 4 fixed to the inner shaft 2. In FIG. 1 and FIG. 2, a proximal end of the electrode needle 4 and a distal end of the conductive line 5 is connected to each other.

FIG. 1 shows a condition where the needle tube 3 and the electrode needle 4 are not projected from a distal part of the outer shaft 1, and FIG. 2 shows a condition where the needle tube 3 and the electrode needle 4 are projected from the distal part of the outer shaft 1. A perspective view of a distal part of the electrotherapy device 100 shown in FIG. 2 is shown in FIG. 3. Note that while the needle tube 3 and a pair of the electrode needles 4 do not align in a line as shown in FIG. 3, the needle tube 3 and the pair of the electrode needles 4 are shown in the same cross-section to be placed alongside in the cross-sectional views of FIG. 1 and FIG. 2 for convenience in drawing.

The outer shaft 1 and the inner shaft 2 are not fixed to each other, and they can move relative to each other in the distal-proximal direction. Accordingly, by pulling the outer shaft 1 to the proximal side, or by pushing the inner shaft 2 to the distal side, or by pushing the inner shaft 2 to the distal side while pulling the outer shaft 1 to the proximal side, the needle tube 3 and the electrode needle 4 become capable of projecting and retracting from the distal part of the outer shaft 1.

The electrotherapy device 100 may be delivered to a treatment site under the condition where the needle tube 3 and the electrode needle 4 are not projected from the distal part of the outer shaft 1 as shown in FIG. 1, and then the needle tube 3 and the electrode needle 4 may be made projected from the distal part of the outer shaft 1 as shown in FIG. 2 at the treatment site. The electrotherapy device 100 is delivered to a treatment site from a body surface through body lumens including a blood vessel and a digestive tract. The electrotherapy device 100 may be directly inserted into a body lumen, or may be used with other devices such as an endoscope. A coating may be applied to the surface of the outer shaft 1 in order to make it easy to pass through a body lumen or a lumen of an endoscope. A coating may be also applied to the surface of the inner shaft 2 in order to make it easy to smoothly move in the outer shaft 1. At a treatment site, medicine and the like may be injected from the needle tube 3 into the body before electrical field is applied from the electrode needle 4, or medicine and the like may be injected from the needle tube 3 into the body while electrical field is being applied from the electrode needle 4, or medicine and the like may be injected before electrical field is applied. Since the needle tube 3 can puncture deep inside of the body with the electrotherapy device 100 of the present invention, medicine and the like can be injected into deep inside of the body.

The location of a distal end of the electrode needle 4 and a distal end of the needle tube 3 may be the same, however, the distal end of the electrode needle 4 is preferably disposed distal to the distal end of the needle tube 3. Such a configuration makes it possible for the electrode needle 4 to be inserted into a site to be treated deeper than the needle tube 3. In the case where medicine injected from the needle tube 3 migrates to a side in the body deeper than the distal end of the needle tube 3, electrical field generated by the electrode needle 4 can be applied to the medicine more appropriately.

Next, other constitutional example of the distal part of the electrotherapy device according to the present invention will be described in reference to FIG. 4. The same reference sign is provided to the same part as the above figures to avoid repeated explanation.

While the configuration where the needle tube 3 is connected to the lumen 11 formed in the inner shaft 2 is shown in the above FIG. 1 to FIG. 3, a tubular body 6, for example shown in FIG. 4, may be connected to a proximal end part of the needle tube 3. Such a configuration can suitably prevent medicine and the like, which is transferred from the inside of the inner shaft 2 to the needle tube 3, from leaking. A proximal end of the inner shaft 2 and a proximal end of the tubular body 6 are preferably disposed in a handle connected to the proximal side of the inner shaft 2. Furthermore, the proximal end of the inner shaft 2 and the proximal end of the tubular body 6 are preferably connected to a medicine inlet provided at the handle, which makes it easier for medicine to be injected. For example, in a case where the inner shaft 2 has one lumen, the tubular body 6 and the conductive line 5 of the linear conductor may be disposed in the lumen. Fixing the conductive line 5 to an inner wall of the inner shaft 2 or the tubular body 6 can prevent the conductive line 5 from getting entangled, while the entanglement otherwise possibly occurs when the electrotherapy device 100 is operated.

The linear conductor includes the electrode needle 4 and the conductive line 5. The electrode needle 4 and the conductive line 5 may be composed of one component, or may be composed of two or more component, such as a needle and a conductive line. A part located distal to the distal end of the inner shaft 2 can be defined to be as the electrode needle 4. A proximal part of the linear conductor or a proximal part of the conductive line 5 can be connected to an electric source to generate electrical field between the electrode needles 4.

The conductive line 5 may be connected to the proximal part of the electrode needle 4, whereas a conductive line may not be connected to the proximal part of the needle tube 3. Such a configuration can lead to improved insulation properties of the needle tube 3.

To improve insulation properties of the needle tube 3, an insulating layer may be disposed outside the needle tube 3. To improve insulation properties of the conductive line 5, an insulating layer may be disposed outside the conductive line 5. The insulating layer can be formed with commonly known insulating materials.

A distal end part of the electrode needle 4 may or may not puncture biological tissue. A configuration where more proximal side of the electrode needle 4 is capable of puncturing biological tissue makes it possible for electrical field to be applied to deep inside of the body.

The electrotherapy device 100 of the present invention preferably has at least two electrode needles 4, and a distance between the two electrode needles 4 preferably is shortened toward the distal end of the electrode needle 4. Especially, in the case where the electrode needle 4 is configured so as to be capable of puncturing biological tissue, forming the electrode needles 4 into a shape that narrows toward the distal end of the electrode needle 4 makes it easy for them to puncture a treatment site.

The conductive line 5 may be fixed to the inner shaft 2. Fixing the conductive line 5 to the inner shaft 2 can prevent the conductive line 5 from, for example, getting entangled.

The electrode needle 4 and the conductive line 5 may be formed from different materials or may be formed from the same material.

The electrode needle 4 and the conductive line 5 may be a single component, or the electrode needle 4 is a separate component from the conductive line 5, or the electrode needle 4 and the conductive line 5 may be indirectly connected to each other.

Materials constituting the electrode needle 4 and the conductive line 5 include, for example, stainless steel, tungsten, copper, and a conductive alloy. The surface of the electrode needle 4 and/or the surface of the conductive line 5 may be plated, and the plating includes, for example, gold plating and platinum plating.

The linear conductor including the electrode needle 4 and the conductive line 5 may have a linear shape without a bent, or may have a flare shape in which the distal end part of the electrode needle 4 spreads out. However, as shown in FIG. 4, the linear conductor preferably has a first bent 21 being convex toward an inner side of the electrotherapy device 100, and a second bent 22 being convex toward an outer side of the electrotherapy device 100 and located at a distal side of the first bent 21. The first bent 21 and the second bent 22 make the distal end part of the electrode needle 4 spread out widely, which enables electrical field to be applied to wider region. In addition, in a condition where the distal end of the inner shaft 2 is located distal to the distal end of the outer shaft 1, the distal end of the needle tube 3 is preferably located distal to the first bent 21. Such a configuration of the needle tube 3 makes it easier for the needle tube 3 to puncture deep inside of the body.

The inner shaft 2 has a first lumen, a second lumen, and a third lumen therein, and a proximal end of the needle tube 3 may be disposed in the first lumen and each of the conductive line 5 may be disposed in the second lumen and the third lumen. Such a configuration can further improve insulation properties of the conductive line 5 of the linear conductor. Electrical field applied by the electrode needle 4 to a site to be treated may be either a bipolar form or a monopolar form. In the case of the bipolar form, disposing the conductive line 5 of the linear conductor in different lumen for different pole can further improve insulation properties. Furthermore, thanks to the inner shaft 2 having a plurality of lumens therein, for example three lumens, the linear conductor and the needle tube 3 can be surely disposed in different places, and therefore, it becomes unlikely for electricity and liquid in the electrotherapy device 100 to contact with each other.

As shown in FIG. 4, the tubular body 6 may be connected to the proximal end part of the needle tube 3, or alternatively, the needle tube 3 may be directly fixed to the distal end of the first lumen, and medicine and the like may be directly pass through the first lumen. The inner structure of the inner shaft 2 in the configuration where the tubular body 6 is connected will be described in reference to FIG. 5A. FIG. 5A is a cross-sectional view taken along the line III-III of the electrotherapy device 100 shown in FIG. 4. The inner shaft 2 has a first lumen 31, a second lumen 32, and a third lumen 33.

In the first lumen 31 at the site of the line III-III shown in FIG. 4, the tubular body 6 is disposed, and the tubular body 6 and the first lumen 31 are not fixed to each other. In the second lumen 32 and the third lumen 33 at the site of the line III-III shown in FIG. 4, each of the conductive line 5 is disposed respectively, and each of the conductive line 5 is not fixed to the second lumen 32 and the third lumen 33.

A cross-sectional view at the distal end of the inner shaft 2 of the electrotherapy device 100 shown in FIG. 4, which is a cross-sectional view taken along the line IV-IV of FIG. 4, is shown in FIG. 5B. At the site of the line IV-IV, the needle tube 3 is disposed in the first lumen 31, and the needle tube 3 and the first lumen 31 are fixed to each other. In the second lumen 32 and the third lumen 33 at the site of the line IV-IV shown in FIG. 4, the electrode needles 4 are disposed respectively, and the electrode needles 4 are fixed to the second lumen 32 and the third lumen 33.

A distance d' between a distal end part of the needle tube 3 and a line connecting the linear conductor (an electrode needle 4) disposed in the second lumen 32 and the linear conductor (an electrode needle 4) disposed in the third lumen 33 in the cross-section IV perpendicular to the distal-proximal direction at a distal end of the needle tube 3 is preferably shorter than a distance d between a center of the first lumen 31 and a line connecting a center of the second lumen 32 and a center of the third lumen 33 in the cross-section III perpendicular to the distal-proximal direction at a position 3 cm proximal from a distal end of the inner shaft 2, as shown in FIGS. 4, 5A and 5C. Such a configuration enables medicine and the like to be injected between the electrode needles 4.

While pulse parameters applied to the electrode needle 4 differs depending on treatment conditions, for instance, a magnetic field strength may be 1 V/cm to 2000 V/cm, a pulse length may be 0.1 mm to 10.0 mm, a number of pulses may be 2 to 20, and a pulse frequency may be 1 Hz to 5 Hz.

At a distal end part of the outer shaft 1 and/or a distal end part of the inner shaft 2, a radiopaque marker is preferably disposed in order to confirm the location of the needle tube 3 and the electrode needle 4 under fluoroscopy. Thanks to the radiopaque marker, the location of the distal end part of the outer shaft 1 and/or the distal end part of the inner shaft 2, which have the radiopaque marker, can be confirmed under fluoroscopy, and therefore, for example, a depth of penetration of the needle tube 3 can be adjusted.

The radiopaque marker preferably has a tubular shape including, for example, a cylindrical shape, a polygonal tubular shape, a shape having a C-shaped cross section formed by cutting a tube, and a coiled shape formed by coiling a wire. Of these, the cylindrical shape is preferable. The radiopaque marker having such a configuration can make it easier for the radiopaque marker to be confirmed under fluoroscopy. Note that the shape of the radiopaque marker disposed at the distal end part of the outer shaft 1 and the distal end part of the inner shaft 2 may be the same or different from each other.

The radiopaque marker may be formed from radiopaque materials including, for example, lead, barium, iodine, tungsten, aurum, platinum, iridium, stainless steel, titanium, and cobalt-chromium alloy. Of these, platinum is more preferable for the radiopaque materials. The radiopaque marker having such a configuration can improve radiographic properties of fluoroscopy. Note that the material of the radiopaque marker disposed at the distal end part of the outer shaft 1 and the distal end part of the inner shaft 2 may be different from each other, however, preferably the same. Using the same material for the radiopaque marker disposed at the distal end part of the outer shaft 1 and the radiopaque marker disposed at the distal end part of the inner shaft 2 can make the visibility of the radiopaque markers similar, which makes it easier for the location of an end part of the needle tube 3, the electrode needle 4, the outer shaft 1, and the like to be confirmed.

The present application claims priority based on Japanese Patent Application No. 2018-193126 filed on Oct. 12, 2018. All the contents described in Japanese Patent Application No. 2018-193126 filed on Oct. 12, 2018 are incorporated herein by reference.

DESCRIPTION OF REFERENCE SIGNS

1: outer shaft
2: inner shaft
3: needle tube
4: electrode needle
5: conductive line
6: tubular body
11: lumen
21: first bent
22: second bent
31: first lumen
32: second lumen
33: third lumen
100: electrotherapy device

The invention claimed is:

1. An electrotherapy device, comprising:
an outer shaft having a lumen and extending in a longitudinal direction from a proximal end to a distal end;
an inner shaft disposed in the lumen of the outer shaft;
a needle tube fixed to the inner shaft;
a first linear conductor comprising a first conductive line and a first electrode needle, the first conductive line connected to a proximal part of the first electrode needle; and
a second linear conductor comprising a second conductive line and a second electrode needle, the second conductive line connected to a proximal part of the second electrode needle, wherein
each of the first electrode needle and the second electrode needle is fixed to a distal portion of the inner shaft,
the inner shaft has a first lumen, a second lumen, and a third lumen,
a proximal end of the needle tube is disposed in the first lumen,
the first conductive line is disposed in the second lumen and the second conductive line is disposed in the third lumen, and
the inner shaft and the outer shaft are configured such that the needle tube and the electrode needles project or retract from a distal part of the outer shaft in the longitudinal direction.

2. The electrotherapy device according to claim 1, wherein a distal end of each of the electrode needles is disposed more distal than a distal end of the needle tube.

3. The electrotherapy device according to claim 1, wherein each of the conductive lines is not connected to a proximal part of the needle tube.

4. The electrotherapy device according to claim 1, wherein the electrode needles and the conductive lines are formed from the same material.

5. The electrotherapy device according to claim 1, further comprising a tubular body connected to a proximal end part of the needle tube.

6. The electrotherapy device according to claim 1, wherein each of the conductive lines is fixed to the inner shaft.

7. The electrotherapy device according to claim 1, wherein
each of the linear conductors has a first bent being convex toward an inner side of the electrotherapy device, and a second bent being convex toward an outer side of the electrotherapy device and located at a distal side of the first bent; and
in a condition where a distal end of the inner shaft is located distal to a distal end of the outer shaft, a distal end of the needle tube is located distal to the first bent.

8. The electrotherapy device according to claim 1, wherein a distance between the first electrode needle and the second electrode needle is enlarged or shortened as the first and second electrode needles extend from a distal end of the inner shaft to the distal end of each of the first and second electrode needles.

9. The electrotherapy device according to claim 1, wherein
a distance between a distal end part of the needle tube and a line connecting the first linear conductor disposed in the second lumen and the second linear conductor disposed in the third lumen in a cross-section perpendicular to the longitudinal direction at a distal end of the needle tube is shorter than a distance between a center of the first lumen and a line connecting a center of the second lumen and a center of the third lumen in a cross-section perpendicular to the longitudinal direction at a position 3 cm proximal from a distal end of the inner shaft.

10. The electrotherapy device according to claim 1, wherein the electrode needles are configured to puncture biological tissue.

11. An electrotherapy device, comprising:
an outer shaft having a lumen and extending in a longitudinal direction from a proximal end to a distal end;
an inner shaft disposed in the lumen of the outer shaft;
a needle tube fixed to the inner shaft; and
a linear conductor having an electrode needle fixed to the inner shaft and having a conductive line connected to a proximal part of the electrode needle,
the inner shaft having a first lumen, and a second lumen,
a proximal end of the needle tube disposed in the first lumen,
the conductive line disposed in the second lumen, and
the outer shaft and the inner shaft configured such that the needle tube and the electrode needle project or retract from a distal part of the outer shaft in the longitudinal direction.

12. An electrotherapy device according to claim 1, wherein relative positions of the needle tube and the first and second electrode needles in the longitudinal direction are maintained before and after the needle tube and the first and second electrode needles are protruded from the distal end of the outer shaft.

13. An electrotherapy device according to claim 1, wherein in a condition where a distal end of the inner shaft is located distal to the distal end of the outer shaft, a distal end of each of the electrode needles is disposed more distal than a distal end of the needle tube.

* * * * *